United States Patent
Noh et al.

(10) Patent No.: US 7,259,005 B2
(45) Date of Patent: *Aug. 21, 2007

(54) MICROORGANISM HAVING ABILITY TO CONVERT STEROL INTO ANDROST-4-ENE-3, 17-DIONE/ANDROSTA-1,4-DIENE-3, 17-DIONE AND PREPARATION METHOD AND USE THEREOF

(75) Inventors: Seung-Kwon Noh, Seoul (KR);
Myung-Kuk Kim, Seoul (KR);
Won-Tae Yoon, Seoul (KR);
Kyung-Moon Park, Gyeonggi-do (KR); Sang-Ok Park, Seoul (KR)

(73) Assignee: Eugene Science Inc., Seoul (KR)

( * ) Notice: Subject to any disclaimer, the term of this patent is extended or adjusted under 35 U.S.C. 154(b) by 497 days.

This patent is subject to a terminal disclaimer.

(21) Appl. No.: 10/477,447

(22) PCT Filed: May 10, 2002

(86) PCT No.: PCT/KR02/00875

§ 371 (c)(1),
(2), (4) Date: Nov. 10, 2003

(87) PCT Pub. No.: WO02/092789

PCT Pub. Date: Nov. 21, 2002

(65) Prior Publication Data

US 2004/0137555 A1   Jul. 15, 2004

(30) Foreign Application Priority Data

May 11, 2001  (KR) ............................. 2001-25702

(51) Int. Cl.
*C12P 33/00* (2006.01)
*C12P 33/20* (2006.01)
*C12P 33/16* (2006.01)
*C12N 1/20* (2006.01)

(52) U.S. Cl. ............... 435/253.1; 435/52; 435/53; 435/55; 435/252.1; 435/252.3

(58) Field of Classification Search ............ 435/253.1, 435/52, 53, 55, 252.1, 252.3
See application file for complete search history.

(56) References Cited

U.S. PATENT DOCUMENTS

| 4,100,027 | A | * | 7/1978 | Weber et al. | ............... 435/55 |
| 4,170,518 | A | * | 10/1979 | Weber et al. | ............... 435/55 |
| 4,293,644 | A |   | 10/1981 | Wovcha et al. | |
| 4,293,645 | A | * | 10/1981 | Wovcha et al. | ............... 435/55 |
| 4,345,029 | A | * | 8/1982 | Wovcha et al. | ............... 435/55 |
| 4,397,946 | A | * | 8/1983 | Imada et al. | ............... 435/55 |
| 5,418,145 | A | * | 5/1995 | Weber et al. | ............... 435/55 |
| 5,516,649 | A | * | 5/1996 | Weber et al. | ............... 435/55 |
| 2004/0152153 | A1 | * | 8/2004 | Noh et al. | ............... 435/52 |

FOREIGN PATENT DOCUMENTS

| JP | 54059395 A | 5/1979 |
| JP | 56120698 A | 9/1981 |

* cited by examiner

*Primary Examiner*—Herbert J. Lilling
(74) *Attorney, Agent, or Firm*—Drinker Biddle & Reath LLP; Daniel A. Monaco

(57) ABSTRACT

Disclosed is a microorganism having an excellent ability to convert sterol into and rost-4-ene-3,17-dione (AD) and androsta-1,4-diene-3,17-dione (ADD), a method for preparation of the microorganism and use thereof, and more particularly, a mutant strain of *Mycobacterium fortuitum* ATCC 29472, *Mycobacterium fortuitum* EUG-119, a method for preparation of the mutant and use thereof in preparing AD and ADD. The mutant of the present invention has an excellent ability to convent sterol into AD and ADD which are steroid hormone precursors, compared with the known microorganisms and accordingly, is very useful for mass production of steroid hormones.

5 Claims, 1 Drawing Sheet

MICROORGANISM HAVING ABILITY TO CONVERT STEROL INTO ANDROST-4-ENE-3, 17-DIONE/ANDROSTA-1,4-DIENE-3, 17-DIONE AND PREPARATION METHOD AND USE THEREOF

TECHNICAL FIELD

The present invention relates to a microorganism, *Mycobacterium fortuitum* EUG-119, having an excellent ability to convert sterol into androst-4-ene-3,17-dione and androsta-1,4-diene-3,17-dione, a method for preparation of the microorganism and use thereof, and more particularly, to a microorganism having four or more times higher conversion rate than that of previously known microorganisms, a method for preparation of the microorganism and use thereof in preparing androst-4-ene-3,17-dione and androsta-1,4-diene-3,17-dione.

PRIOR ART

Steroids, which are secretary hormones released from the adrenal cortex, the testicle, the ovary or the placenta, the corpus luteum are synthesized from cholesterol. They are classified into about five classes according to their physiological activities, as follows: sex hormones of androgen (androsterone, testosterone, etc.) and estrogen (estradiol, etc.) playing a critical role in the development of secondary sex characteristics in men and women, respectively, gestogen (progesterone, etc.) stimulating and maintaining pregnancy, glucocorticoid (cortisone, hydrocortisone, etc.) stimulating gluconeogenesis and increasing liver glycogen levels by catabolism of proteins, and mineralcorticoid (deoxycorticosterone, aldosterone, etc.) playing a important role in maintaining the balance of electrolytes and water in a body.

Levels of the above hormones become unbalanced in a body owing to increased stresses and exposure to environmental hormones in accordance with the advance of civilization, resulting in occurrence of many diseases, and widespread use of the steroid hormones is conducted for therapy of the diseases. In particular, synthesized estrogens are essentially used in artificial fertilization and therapy of sterile patients, and glucocorticoids play a role in relieving the pain caused by various inflammations, such as iriditis, arthritis and the like. In addition, Addison's disease, which is fatal, can be treated by administration of deoxycorticosterone and hydrocortisone.

There have been conducted a variety of researches into in vitro synthesis of steroid hormones to meet the increased demands as described above, and one of them relates to production of steroid hormone precursors using a microorganism. Mamoli and Vercellone (Ber. 70470 and Ber. 702079, 1937) reported reduction of 17-ketosteroids to 17-β-hydroxysteroid by fermentation of yeast. Also, Peterson and Murray in U.S. Pat. No. 2,602,769 disclosed a method for producing 11α-hydroxylation of progesterone using the fungus of genus *Rhizopus*, and Kraychy in U.S. Pat. No. 3,684,657 disclosed a process for androst4-ene-diene-3,17-dione, androsta-1,4-diene-3,17-dione, and 20α-hydroxymethylpregna-1,4-dien-3-one from a steroid comprising a 17-alkyl using *Mycobacterium* species.

To achieve mass production of steroid hormones, there were attempts to isolate microorganisms using sterols as a sole carbon source and to modify structure of the sterol used as a substrate for fermentation, and also, to enhance an acquisition rate of steroids with the use of chemical additives capable of preventing degradation of sterol nucleus, such as a metal, a metal absorbent and a metal reducing agent, have made great progress (Marsheck, et. al., Applied microbiology. 23(1). 72-77, 1972). Moreover, there were also performed researches for improving productivity of steroid precursors, in which mutagenesis was performed on microorganisms isolated from soil through physical and chemical treatments, and particularly, Upjohn in U.S. Pat. No. 4,293,644 described a method for yield-up androst-4-ene-3,17-dione (hereinafter referred to as AD) predominantly and a small amount of androsta-1,4-diene-3,17-dione (hereinafter referred to as ADD) from a variety of sterols by a mutant strain from *Mycobacterium* (ATCC 29472).

In accordance with increased demands for steroid hormone medicines, there is a need for mass production of the above mentioned hormone precursors, especially AD and ADD, which are important precursor compounds for in vitro synthesis of steroids. However, the previously known microorganisms have low productivity in synthesizing AD and ADD. With this regard, it is urgently required to develop microorganisms having a high conversion rate of sterols into AD and ADD.

DISCLOSURE OF THE INVENTION

As a result of many trials by the inventors of the present invention, it was found that a *Mycobacterium fortuitum* EUG-119 mutant strain of *Mycobacterium fortuitum* (ATCC 29472), has an excellent conversion efficiency of sterols into AD and ADD, and the present invention was accomplished on the basis of the result.

Accordingly, it is an object of the present invention to provide a mutant microorganism having an excellent conversion efficiency of sterols into AD and ADD.

It is another object of the present invention to provide a method for preparing a mutant microorganism having an excellent conversion efficiency of sterols into AD and ADD.

It is still another object of the present invention to provide a method for preparing AD and ADD using a mutant microorganism having an excellent conversion efficiency of sterols into AD and ADD.

To achieve the above objects, the present invention provides a method for preparing *Mycobacterium fortuitum* EUG-119, deposited in the Korean Culture Center of Microorganisms (KCCM) with accession No. KCCM-10259, comprising the steps of: (a) culturing *Mycobacterium fortuitum* ATCC 29472 strain in a sterol-containing culture medium; (b) treating the cultured *Mycobacterium fortuitum* with nitrosoguanidine (NTG); and (c) growing the nitrosoguanidine-treated bacteria in a medium supplemented with sterol or AD and ADD at a concentration of 0.1-2.0 g/L, whereby mutant strains growing rapidly in a sterol-adding medium and slowly in an AD and ADD-adding medium can be selected.

A method for preparing AD and ADD of the present invention comprises steps of culturing the mutant microorganism, *Mycobacterium fortuitum* EUG-119, in a sterol-containing liquid medium and recovering AD and ADD from the cultivated medium.

BEST MODES FOR CARRYING OUT THE INVENTION

Figure 1:
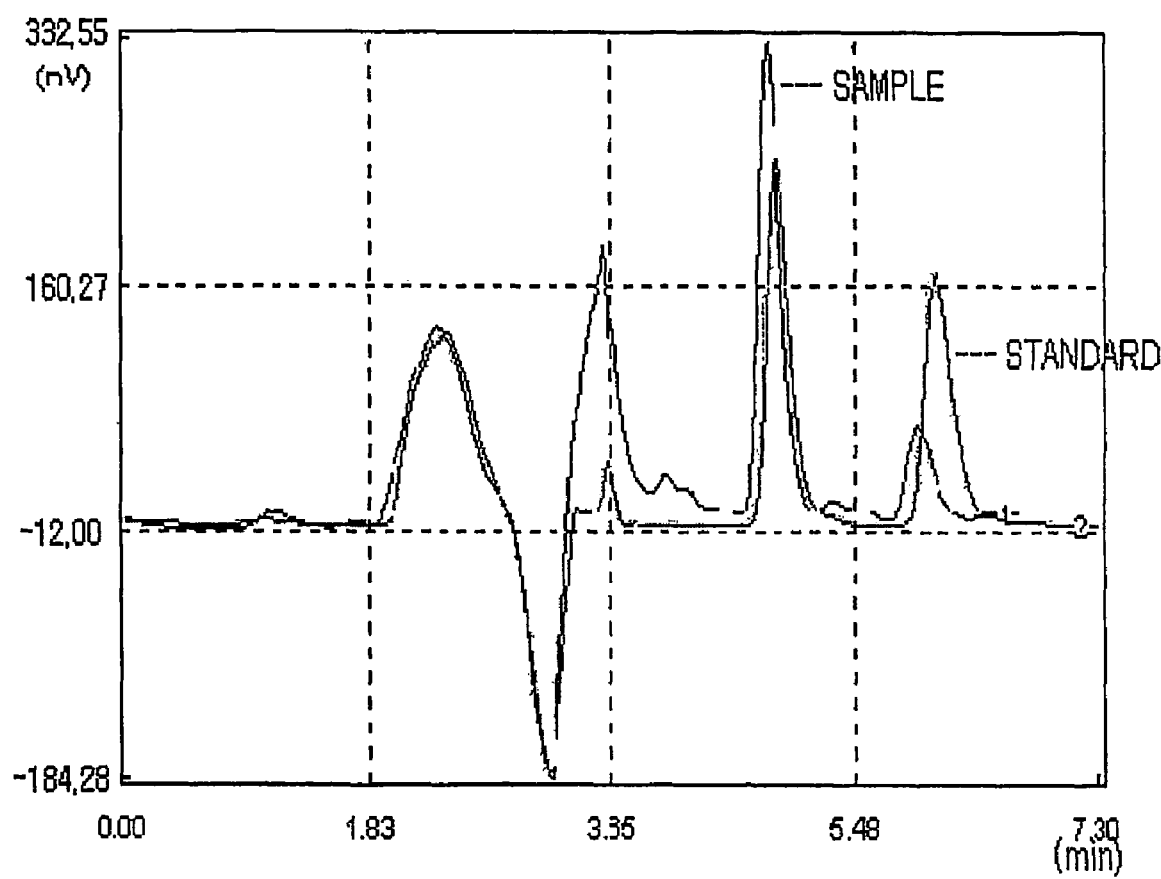
FIG. 1 is a HPLC chromatogram of AD and ADD in the cultured medium of *Mycobacterium fortuitum* EUG-119.

In accordance with the present invention, there was used *Mycobacterium fortuitum* (ATCC 29472), which is capable of transforming to steroids from cholesterols by fermentation.

To prepare *Mycobacterium fortuitum* EUG-119 of the present invention, at first, *Mycobacterium fortuitum* strain (ATCC 29472) was grown to O.D. 0.6 to 0.8, and then treated with nitrosoguanidine (NTG) at an amount capable of killing 99.9% of organisms. NTG, which is a compound commonly used in producing mutant strains of microorganisms, induces mutations through substitution of GC pair with AT pair during DNA replication by methylation at $C_6$ of guanine. The amount of NTG is 300 to 400 µg per 5 ml of medium, and the preferred amount is 330 µg per 5 ml. In addition, the mutation can be accomplished by UV irradiation, INH (Isoniazid) and other mutagenic compounds.

From the NTG-treated strains, there were selected mutant strains having both a high growth rate on a sterol-adding solid medium and a low growth rate on a AD and ADD-adding solid medium, and finally, a mutant strain *Mycobacterium fortuitum* EUG-119 having the highest conversion rate was obtained through the flask cultivation.

Preferably, sterol or AD and ADD used in the strain selection is added to a medium at an amount of 0.1 to 2.0 g/L, and preferably, 0.4 to 0.6 g/L. Sterol can be selected from the group consisting of sitosterol, cholesterol, stigmasterol and campesterol, and it is preferable that the sterol is from cholesterol.

*Mycobacterium fortuitum* EUG-119 prepared by the method as described above was deposited in Korean Culture Center of Microorganisms with accession No. KCCM 10259 on Apr. 14, 2001.

In an embodiment of the present invention, in which the finally selected mutant strain, *Mycobacterium fortuitum* EUG-119 was incubated and its conversion rate of cholesterol into AD and ADD was analyzed, the mutant strain showed about 2.3 times higher conversion rate in a small scale cultivation and about 4.2 times higher in a large scale cultivation, than a wild type strain. AD and ADD were recovered at a purification yield of about 80% from 2 L of the mutant strain-cultivated medium by common separation and purification processes. It was found that, 2 days after cultivation, the mutant strain produced higher concentrations of AD and ADD than the wild strain.

Accordingly, *Mycobacterium fortuitum* EUG-119 of the present invention can be used for mass production of AD and ADD. Such a method comprises the steps of culturing *Mycobacterium fortuitum* EUG-119 in a sterol-containing liquid medium and recovering AD and ADD from the cultivated medium.

When *Mycobacterium fortuitum* EUG-119 of the present invention is used in preparing AD and ADD used as a precursor for steroid hormone synthesis, AD and ADD can be obtained at a high yield.

The present invention will be explained in more detail with reference to the following examples in conjunction with the accompanying drawing. However, the following examples are provided only to illustrate the present invention, and the present invention is not limited to them.

EXAMPLE 1

Preparation of Mutant Strains

To induce mutation, *Mycobacterium fortuitum* strain (ATCC 29472) was inoculated in YNG medium, and cultured upon reaching O.D. 0.6 to 0.8, 5 ml of the cultured medium was centrifuged, obtaining a cell pellet. The obtained pellet was washed twice with sterilized 0.1 M sodium citrate buffer (pH 5.6) containing 0.5% Tween 80, and resuspended in 5 ml of the buffer, and NTG was added to the cell suspension at a concentration of 330 µg/ml. NTG-treated cell suspension was incubated with shaking at 37° C. for 90 min, and then centrifuged, obtaining a cell pellet and the obtained cell pellet was washed three times with a sterilized 0.1 M sodium phosphate buffer (pH 7.0) and resuspended in the buffer. The final cell suspension was loaded onto a SMI solid medium and incubated at 37° C. for 3-4 days to form colonies.

EXAMPLE 2

Selection of Mutant Strains

Colonies obtained from Example 1 were inoculated in MS1, MS1+cholesterol, MS1+ADD (or AD) and YNG solid media and incubated at 30° C. for 3 days to select a strain having both high growth rate in cholesterol-containing medium (MS1+cholesterol medium) and a low growth rate in ADD (or AD)-containing medium, and the selected strain was designated as *Mycobacterium fortuitum* EUG-119. The MS1 medium, a minimum inorganic medium, was used as a control, and compositions of the media are shown in Table 1.

TABLE 1

| | Culture medium (%) | | | |
|---|---|---|---|---|
| Ingredient | YNG | SM1 | MS1 | SM4 (Fermentation medium) |
| Yeast extract | 0.1 | — | — | 0.5 |
| Nutritional broth | 0.8 | — | — | — |
| Glycerol | 0.5 | 1 | — | — |
| Tween 80 | 0.1 | — | — | 0.01 |
| NaCl | — | — | 0.0005 | — |
| $K_2HPO_4$ | — | 0.05 | 0.02 | 0.04 |
| $KH_2PO_4$ | — | — | — | 0.08 |
| $NH_4Cl$ | — | 0.1 | — | — |
| $MgSO_4 7H_2O$ | — | 0.05 | 0.25 | 0.2 |
| $FeCl_3 6H_2O$ | — | 0.005 | — | — |
| $NH_4NO_3$ | — | — | 0.1 | — |
| $FeSO_4 7H_2O$ | — | — | 0.0001 | 0.0005 |
| Ammonium acetate | — | — | — | 0.15 |
| $ZnSO_4 7H_2O$ | — | — | — | 0.0002 |
| $MnCl_4 4H_2O$ | — | — | — | 0.00005 |
| Glucose | — | — | — | 1 |
| Agar | — | 1.5 | 1.5 | — |
| pH | 7.0 | — | — | 7.5 |

EXAMPLE 3

Investigation for Conversion Rate of Cholesterol into AD and ADD in *M. fortuitum* EUG-119 Strain Mutant strain, *M. fortuitum* EUG-119, selected from Example 2 was pre-cultured in 5 ml of YNG medium, and then cultivated at 30° C. for 120 hours at 200 rpm in 100 ml SM4 fermentation medium (refer to Table 1) containing 1 g glucose, 0.5 g yeast extract, 0.01 g Tween 80 and various inorganic salts. Cholesterol was dissolved with acetone, because it is not dissolved well in culture media, and cholesterol suspension in acetone was added to the medium at an amount of 0.1 g cholesterol per 100 ml. After the incubation, cultured media were extracted with ethyl ether and petroleum ether and then dissolved with 2-propanol, and used in an analysis of amounts of AD and ADD produced by *M. fortuitum* EUG-119 strain from cholesterol, which was carried out by high pressure liquid chromatography (HPLC). A conversion rate of cholesterol into AD and ADD was represented as yield calculated by a ratio of molar concentration of AD and ADD and molar concentration of added cholesterol. Also, there were investigated produced amounts of AD and ADD and a conversion rate of wild strain, *M. fortuitum* (ATCC 29472). The results are shown in Table 2.

TABLE 2

|  | Wild strain | *M. fortuitum* EUG-119 |
| --- | --- | --- |
| Yield (Molar %) | 27 | 64 |
| Produced amounts of AD and ADD (mg/L) | 199 | 472 |

Note:
Yield = Molar concentration of produced AD and ADD/Molar concentration of added cholesterol As shown in Table 2, mutant strain, *M. fortuitum* EUG-119 showed about 2.3 times higher conversion rate of cholesterol into AD and ADD than wild strain, *M. fortuitum* ATCC 29472.

EXAMPLE 4

Mutant strain pre-cultured in 100 ml medium, prepared by the same method as Example 3, was inoculated into a 5 L fermentor containing sterilized 2.5 L medium (pH 8.0) and incubated at 1 vvm(aeration flow rate) for 120 hours at 30° C. with shaking at 600 rpm. Cholesterol dissolved in acetone was added to at an amount of 5 g/L. Produced amounts of AD and ADD and conversion rate of cholesterol into AD and ADD were analyzed by the same method as Example 3, and the results are shown in Table 3.

TABLE 3

|  | Wild strain | *M. fortuitum* EUG-119 |
| --- | --- | --- |
| Yield (Molar %) | 14 | 59 |
| Produced amounts of AD and ADD (mg/L) | 510 | 2,177 |

As shown in Table 3, the mutant strain, *M. fortuitum* EUG-119, exhibited about 4.2 times higher conversion rate than the wild strain.

EXAMPLE 5

AD and ADD were purified from the culture broth prepared in Example 4. 2.5 L of the culture broth was adjusted to pH 3.0 and centrifuged at 5000 rpm for 10 min at 4° C. The resulting biomass pellet was extracted by suspension in 70% acetone and filtered, and after evaporation of acetone, held at 5-10° C., allowing precipitation of hormones. The resulting precipitate was filtered and dried at 55° C., and the dried precipitate was added with hexane to remove remaining cholesterol, and then filtered and dried again, and the resulting crude hormone intermediates were recovered. Recovery yields for hormone intermediates are shown in Table 4.

TABLE 4

|  | Weight (g) of biomass | Yield (%) |
| --- | --- | --- |
| Culture broth | 5.2 | 100 |
| After acetone extraction | 4.6 | 88 |
| Crude hormones | 4.2 | 81 |

As shown in Table 4, purification yield of hormone intermediates was about 80% from the 2.5 L culture broth of the mutant strain, *M. fortuitum* EUG-119.

EXAMPLE 6

The hormone intermediates produced by a wild type of *M. fortuitum* and a mutant strain, *M. fortuitum* EUG-119, were measured for concentration using HPLC. The culture broth medium containing the wild type or the mutant type of *M. fortuitum*, was extracted twice with four volumes of a mixture of diethyl ether and petroleum ether in a ratio of 1:1, and the solvents were then evaporated. The extracted hormones were suspended in isopropyl alcohol for quantitative analysis, with resort to HPLC utilizing Pegasil ODS (4.6× 250, 5 μm, 120 Å, Senshu Pak, Japan) as a column under conditions of a flow rate of 1.0 ml/min, 2,700 psi and 250 nm, and the mobile phase was analyzed using 50% THF (refer to FIG. 1).

As a result, it was found that, from 2 days after culturing, the mutant strain, *M. fortuitum* EUG-119, produced AD and ADD in higher levels than the wild strain, *M. fortuitum* ATCC 29472.

EXAMPLE 7

Mycological properties of mutant strain, *Mycobacterium fortuitum* EUG-119, were investigated using the known methods, and are as follows.

*M. fortuitum* EUG-119 can grow at 30-35° C., utilizing sugars including glucose, polysaccharides, glycerol, fatty acids, sterols, and the like as a carbon source. Also, *M. fortuitum* EUG-119, which is a Gram (+) strain, contain abundant fats in its cell wall and grows forming yellow colonies.

As a whole, *M. fortuitum* EUG-119 of the present invention shows similar morphological and physical properties to the known *M. fortuitum* ATCC 29472 strain, but has an excellent ability to convert sterol into AD and ADD by its fermentation action.

INDUSTRIAL APPLICABILITY

As described above, *Mycobacterium fortuitum* EUG-119 of the present invention has an excellent conversion efficiency of sterol to AD and ADD, which can be used as hormone precursors, in comparison with the previously known microorganisms, especially *M. fortuitum* ATCC 29472. Accordingly, *M. fortuitum* EUG-119 of the present invention is greatly useful for mass production of steroid hormones.

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

To: Seung-Kwon Noh
Eugene Science Inc. 16-7,
Samjung-dong, Ohjung-gu,
Bucheon, Kyunggi.
421-150

RECEIPT IN THE CASE OF AN ORIGINAL
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR: *Mycobacterium fortuitum* EUG-119 | Accession number given by the INTERNATIONAL DEPOSITARY AUTHORITY: KCCM-10259 |

| II. SCIENTIFIC DESCRIPTION AND/OR PROPOSED TAXONOMIC DESIGNATION |
|---|
| The microorganism identified under I above was accompanied by: <br> ☐ a scientific description <br> ☐ a proposed taxonomic designation <br> (Mark with a cross where applicable) |

| III. RECEIPT AND ACCEPTANCE |
|---|
| This International Depositary Authority accepts the microorganism identified under I above, which was received by it on Apr. 14, 2001. (date of the original deposit)[1] |

| IV. INTERNATIONAL DEPOSITARY AUTHORITY | |
|---|---|
| Name: Korean Culture Center of Microorganisms <br><br> Address: 361-221, Yurim B/D <br> Hongje 1-dong, <br> Seodaemun-gu <br> SEOUL 120-091 <br> Republic of Korea | Signature(s) of person(s) having the power to represent the International Depositary Authority of of authorized official(s): <br><br> Date: Apr. 19, 2001 |

[1] Where Rule 6.4(d) applies, such date is the date on which the status of international depositary authority was acquired : where a deposit made outside the Budapest Treaty after the acquisition of the status of international depositary authority is converted into a deposit under the Budapest Treaty, such date is the date on which the microorganism was received by the international depositary authority.

Form BP/4                                                                 Sole page

The invention claimed is:

1. The *Mycobacterium fortuitum* cell line deposited as KCCM-10259.

2. A method for preparing *Mycobacterium fortuitum* KCCM-10259, comprising the steps of:
   (a) culturing *Mycobacterium fortuitum* ATCC 29472 strain in a sterol-containing culture medium to reach an optical density of 0.6-0.8;
   (b) treating the cultured *Mycobacterium fortuitum* with nitrosoguanidine at a concentration of 300-400 μg/ml;
   (c) growing the nitrosoguanidine-treated bacteria in a medium supplemented with sterol or androst-4-ene-3,17-dione and androsta-1,4-diene-3,17-dione at a concentration of 0.1-2.0 g/L, whereby mutant strains growing rapidly in a sterol-adding medium and slowly in an androst-4-ene-3,17 dione and androsta-1,4-diene-3,17-dione-adding medium can be selected; and
   (d) obtaining *Mycobacterium fortuitum* KCCM-10259.

3. The method as set forth in claim 2, wherein the sterol is selected from the group consisting of sitosterol, cholesterol, stigmasterol and campesterol.

4. A method for preparing androst-4-ene-3,17-dione and androsta-1,4-diene-3,17-dione, comprising the steps of culturing *Mycobacterium fortuitum* KCCM-10259 in a sterol-containing liquid medium and recovering androst-4-ene-3,17-dione and androsta-1,4-diene-3,17-dione from the cultivated medium.

5. The method as set forth in claim 4 wherein the sterol is selected from the group consisting of sitosterol, cholesterol, stigmasterol and campesterol.

* * * * *